US009581594B2

(12) United States Patent
Taitt et al.

(10) Patent No.: US 9,581,594 B2
(45) Date of Patent: Feb. 28, 2017

(54) PORPHYRIN—MODIFIED ANTIMICROBIAL PEPTIDES FOR APPLICATION AS INDICATORS OF MICROBIAL TARGETS

(71) Applicants: Chris Rowe Taitt, White Plains, MD (US); Brandy J. White, Washington, DC (US)

(72) Inventors: Chris Rowe Taitt, White Plains, MD (US); Brandy J. White, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 334 days.

(21) Appl. No.: 14/208,189

(22) Filed: Mar. 13, 2014

(65) Prior Publication Data

US 2014/0274776 A1    Sep. 18, 2014

Related U.S. Application Data

(60) Provisional application No. 61/784,260, filed on Mar. 14, 2013.

(51) Int. Cl.
| | |
|---|---|
| *G01N 33/569* | (2006.01) |
| *G01N 33/58* | (2006.01) |
| *D06M 10/00* | (2006.01) |
| *D06M 10/08* | (2006.01) |
| *D06M 13/07* | (2006.01) |
| *D06M 13/352* | (2006.01) |
| *D06M 13/513* | (2006.01) |
| *D06M 16/00* | (2006.01) |

(52) U.S. Cl.
CPC ...... *G01N 33/56911* (2013.01); *D06M 10/003* (2013.01); *D06M 10/08* (2013.01); *D06M 13/07* (2013.01); *D06M 13/352* (2013.01); *D06M 13/513* (2013.01); *D06M 13/5135* (2013.01); *D06M 16/00* (2013.01); *G01N 33/582* (2013.01); *D06M 2400/02* (2013.01)

(58) Field of Classification Search
CPC .... D06M 10/003; D06M 10/08; D06M 13/07; D06M 13/352; D06M 13/513; D06M 13/5135; D06M 16/00; D06M 2400/02; G01N 33/56911; G01N 33/582
See application file for complete search history.

(56) References Cited

U.S. PATENT DOCUMENTS

| | | | |
|---|---|---|---|
| 6,462,070 B1 | 10/2002 | Hasan et al. | |
| 6,821,738 B2 | 11/2004 | Harmon | |
| 7,268,155 B2 | 9/2007 | Hasan et al. | |
| 8,658,372 B2 * | 2/2014 | Kulagina | G01N 33/5308 435/7.1 |
| 2002/0183245 A1 * | 12/2002 | Hasan | A61K 41/0019 514/2.3 |
| 2006/0281074 A1 * | 12/2006 | Kulagina | G01N 33/5308 435/5 |
| 2009/0326434 A1 | 12/2009 | Nifantiev et al. | |

OTHER PUBLICATIONS

Salazar-Gonzalez et al., "*Salmonella* flagellin, a microbial target of the innate and adaptive immune system," Immunol. Lett., 2005, vol. 101, No. 2, pp. 117-122.*
Falla et al., "Mode of Action of the Antimicrobial Peptide Indolicidin," J. Biol. Chem., 1996, vol. 271, No. 32, pp. 19298-19303.*
Tsou et al., "Protein surface recognition by porphyrin-based receptors," J. Porphyrins Phthalocyanines, 2004, vol. 8, No. 1-3, pp. 141-147.*
Johnson et al., "Porphyrin—modified antimicrobial peptide indicators for detection of bacteria," Sens. Bio-Sens. Res., 2016, vol. 8, pp. 1-7.*
Gehring et al., "An antibody microarray, in multiwell plate format, for multiplex screening of foodborne pathogenic bacteria and biomolecules," Anal. Bioanal. Chem., 2008, vol. 391, issue 2, pp. 497-506.*
Baldini et al., "Pattern-based detection of different proteins using an array of fluorescent protein surface receptors," J. Am. Chem. Soc., Supporting Information, 2004. vol. 126, No. 18, pp. S1-S7.*
Dosselli et al., "Porphyrin-apidaecin conjugate as a new broad spectrum antibacterial agent" ACS Medicinal Chemistry Letters. vol. 1. No. 1. pp. 35-38 (2010).
Baldini, L., et al., Pattern-based detection of different proteins using an array of fluorescent protein surface receptors. Journal of the American Chemical Society. 2004. 126(18): p. 5656-5657.
Dosselli, R., et al., Synthesis, Characterization, and Photoinduced Antibacterial Activity of Porphyrin-Type Photosensitizers Conjugated to the Antimicrobial Peptide Apidaecin 1b. J. Med. Chem. 2013, 56, 1052?1063.
Harmon, H.J., Specific Visible Spectral Changes Induced by Guanine Binding to Cytosine-derivatized porphyrin. J. Porphyrins Phthalocyanines, 2002. 6: p. 73-77.
Kuciauskas, D., et al., Exciton annihilation and energy transfer in self-assembled peptide-porphryin complexes depends on peptide secondary structure. J Phys Chem B, 2010. 114: p. 16029-16035.
Kulagina, N.V., et al., Antimicrobial peptide-based array for *Escherichia coli* and *Salmonella* screening. Analytica Chimica Acta, 2006. 575(1): p. 9-15.
Kulagina, N.V., et al., Antimicrobial peptides: New recognition molecules for detecting botulinum toxins. Sensors, 2007. 7(11): p. 2808-2824.
Liu F. et al. Lipopolysaccharide neutralizing peptide-porphyrin conjugates for effective photoinactivation and intracellular imaging of Gram-negative bacteria strains. Bioconjug Chem, 2012. 23: p. 1639-1647.
North, S.H., et al. Surface immobilization chemistry influences peptide-based detection of lipopolysaccharide and lipoteichoic acid. Journal of Peptide Science, 2012. 18(6): p. 366-372.

(Continued)

*Primary Examiner* — Galina Yakovleva
(74) *Attorney, Agent, or Firm* — US Naval Research Laboratory; Roy Roberts (57) ABSTRACT

Porphyrin-modified antimicrobial peptides as described here may be used as indicators of the presence of microbial targets. Their application may be as (for example) (1) fluorescent indicators in a microarray format, (2) fluorescence or absorbance based indicators in traditional solution based applications, or (3) reflectance based indicators for use in reagent-less detection platforms.

1 Claim, 5 Drawing Sheets

(56) References Cited

OTHER PUBLICATIONS

Pristovšek, P. and J. Kidric?, Solution Structure of Polymyxins B and E and Effect of Binding to Lipopolysaccharide: An NMR and Molecular Modeling Study. Journal of Medicinal Chemistry, 1999. 42(22): p. 4604-4613.

Rakow, N.A. and K.S. Suslick, A colorimetric sensor array for odour visualization. Nature, 2000. 406(6797): p. 710-713.

Reddi, E., et al., Photophysical properties and antibacterial activity of meso-substituted cationic porphyrins Photochem Photobiol, 2002. 75: p. 462-470.

Sibrian-Vasquez, M., T. Jensen, and M. Vicente, Synthesis, characterization, and metabolic stability of porphyrin-peptide conjugates bearing bifunctional signaling sequences. J Med Chem, 2008. 51: p. 2915-2923.

Taitt, C.R., et al., Array Biosensor for Toxin Detection: Continued Advances. Sensors, 2008. 8(12): p. 8361-8377.

White, B.J. and H.J. Harmon, Interaction of monosulfonate tetraphenyl porphyrin, a competitive inhibitor, with acetylcholinesterase. Biosens Bioelectron, 2002. 17(6-7): p. 463-469.

White, B.J. and H.J. Harmon, Optical solid-state detection of organophosphates using organophosphorus hydrolase. Biosens Bioelectron, 2005. 20(10): p. 1977-1983.

Zhou, H.C., et al., Pattern recognition of proteins based on an array of functionalized porphyrins. Journal of the American Chemical Society, 2006. 128(7): p. 2421-2425.

\* cited by examiner

```
SEQUENCE LISTING

<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: synthetic construct

<400> SEQUENCE: 1

Ile Leu Pro Trp Lys Trp Pro Trp Trp Pro Trp Arg Arg
1               5                   10

<210> SEQ ID NO 2
<211> LENGTH: 26
<212> TYPE: PRT
<213> ORGANISM: Artificial Sequence
<220> FEATURE:
<223> OTHER INFORMATION: synthetic construct

<400> SEQUENCE: 2

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 3
<211> LENGTH: 15
<212> TYPE: PRT
<213> ORGANISM: Artificial Sequence
<220> FEATURE:
<223> OTHER INFORMATION: synthetic construct

<400> SEQUENCE: 3
```

```
Lys Trp Lys Leu Phe Lys Lys Ile Gly Ala Val Leu Lys Val Leu
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (3)..(11)

<400> SEQUENCE: 4

Arg Leu Cys Arg Ile Val Val Ile Arg Val Cys Arg
1               5                   10
```

PORPHYRIN—MODIFIED ANTIMICROBIAL PEPTIDES FOR APPLICATION AS INDICATORS OF MICROBIAL TARGETS

CROSS-REFERENCE TO RELATED APPLICATIONS

This Application claims the benefit of U.S. Provisional Application 61/784,260 filed on Mar. 14, 2013.

BACKGROUND

A need exists for microbial detection techniques suitable to autonomous and/or distributed sensing platforms.

BRIEF SUMMARY

In one embodiment, method of detecting includes providing a porphyrin-modified antimicrobial peptide comprising a porphyrin covalently attached to an antimicrobial peptide; contacting the porphyrin-modified antimicrobial peptide with a microbial target; and detecting a change in fluorescence, absorbance, and/or reflectance of the porphyrin-modified antimicrobial peptide caused by the contacting, wherein the method is operable to detect the microbial targets without use of an additional optically-active reagent.

In another embodiment, a method of detecting includes providing a first porphyrin-modified antimicrobial peptide comprising a porphyrin covalently attached to a first antimicrobial peptide; providing a second porphyrin-modified antimicrobial peptide comprising a porphyrin covalently attached to a second antimicrobial peptide; contacting the first and second porphyrin-modified antimicrobial peptides with a microbial target; and detecting a change in reflectance of the first and second porphyrin-modified antimicrobial peptides caused by the contacting, wherein the method is operable to detect the microbial targets without use of an additional optically-active reagent In a further embodiment, a sensor includes a porphyrin-modified antimicrobial peptide comprising a porphyrin covalently attached to a antimicrobial peptide, wherein the sensor is operable to specifically react to a microbial target via changing fluorescence, absorbance, and/or reflectance properties of the porphyrin-modified antimicrobial peptide specifically upon contact with the microbial target.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Description

Antimicrobial peptides (AMPs) comprise a group of biomolecules that has evolved to recognize and kill target microbes by binding to and disrupting cell membranes. Several unique characteristics of AMPs make them extremely attractive alternatives to antibodies for detection of microbial biothreats: resistance to proteases, stability to environmental extremes, and high affinity, overlapping (but not identical) binding reactions with microbial membranes and membrane components. Arrays of AMPs have been used to detect and classify microbial pathogens with similar or superior sensitivity to antibody based assays; their broad-spectrum binding activities also provide the potential for detection of unknown (or unsuspected) microbes. See refs. 1-5. In each applicable platform, the AMPs mediated target binding and an additional optical "tracer" (e.g., labeled antibody, non-specific dye) was required for signal transduction. This constraint increases the number of reagents required and the overall complexity of assays. Development of an AMP-based material that is capable of both recognition and signal generation without additional reagents or steps is highly desirable, for example for AMP-based detection techniques to autonomous/distributed sensing platforms.

Porphyrins possess a strong absorption band around 400 nm with an extinction coefficient that can exceed 500 mM$^{-1}$ cm$^{-1}$ as well as several less intense bands between 450 and 700 nm. Porphyrins are typically intensely fluorescent with emission bands between 600 and 750 nm and quantum yields of ~0.8-0.9. The intense spectrophotometric characteristics as well as the strong sensitivity of these characteristics to the immediate environment of the molecule result from the twenty-two π-electrons of the parent structure. This sensitivity can be used for reporting changes in the surrounding environment with a high degree of specificity. Modification of the basic porphyrin structure by substituent groups around the periphery of the nearly flat parent structure or through incorporation of a metal in the central position leads to differences in the spectrophotometric characteristics. These difference result from electron withdraw/donation by these groups or through alterations to the degree of conjugation and provided a unique approach to development of molecular beacons.

There have been reports of modification of the porphyrin structures using single amino acids or dipeptides. See refs. 6-8. Changes in porphyrin fluorescence induced by binding of these porphyrin derivatives to proteins were observed. Arrays of these constructs were applied to identification of the proteins. Previous work has shown that porphyrins can also be used to report conformational changes in enzymes upon substrate binding when the porphyrin-enzyme interaction results in mixed-type enzymatic inhibition. See refs. 9 and 10. For application in light harvesting, Kuciauskas et al. (ref. 11) demonstrated that a change in the secondary structure of a synthetic α-helical peptide had a significant effect on the fluorescence spectra and kinetics of a conjugated porphyrin. A further report demonstrated that modification of the periphery of the porphyrin using cytosine resulted in an optical indicator for the presence of guanine (ref. 12).

A number of publications report use of porphyrin-peptide conjugates for targeting and photodestruction of target cells. See refs. 11 and 13-18. Specifically, the native or engineered antimicrobial peptide domain is used to target the peptide-porphyrin conjugate to the appropriate target cell (cancer cell, Gram-negative bacterial pathogen), whereas the porphyrin moiety is used as a source of reactive oxygen species upon illumination. See ref. 19. In such descriptions, the porphyrin entity has been used for photodestruction of cells bound to the conjugate. Porphyrin-peptide conjugates have also been used as imaging agents for microscopic fluorescent examination of cells (for example, see ref. 15), however this does not appear to be specificity or selectivity in the response.

Described herein is the use of antimicrobial peptides modified using porphyrins as an avenue for achieving reagent-less detection and classification of biological targets. The local environment of a covalently attached porphyrin changes following conformational changes in the antimicrobial peptide.

As described herein, two or more peptide-porphyrin conjugates may be used to detect many microbes, with broad classification of the detected cells based on the differential changes in optical properties for each porphyrin-peptide conjugate.

EXAMPLES

Porphyrins

Porphyrins used for conjugation to antimicrobial peptides include 5-mono(4-carboxyphenyl)-10,15,20-triphenyl porphine (C$_1$TPP) and its more water-soluble derivative, meso-tri(4-sulfonatophenyl)mono(4-carboxyphenyl) porphine (C1S3TPP). Other porphyrins may be employed.

Peptides

The peptides chosen for conjugation represent different categories of antimicrobial peptides, preferably those that undergo a conformational change on binding to a target.

Indolicidin (Ind; ILPWKWPWWPWRR-NH$_2$, SEQ ID No: 1) is extended/unstructured in solution, but forms extended boat conformation upon binding lipid vesicles. Also included were two peptides engineered to possess a unique cysteine at the N- or C-terminus (C1-indolicin and C14-indolicin, respectively).

Cecropin A-melittin hybrid peptides CeMe(L): (KWKLFKKIGIGAVLKVLTTGLPALIS-NH$_2$, SEQ ID No: 2) and CeMe(S)-(KWKLFKKIGAVLKVL-NH$_2$, SEQ ID No: 3) represent cationic antimicrobial peptides that are unstructured in solution and undergo a conformational change to form amiphipathic α-helices upon binding to target cells and membranes.

Bactenecin (Bac; RLCRIVVIRVCR; cyclized via disulfide bridge, SEQ ID No: 4) is a small β-structured peptide whose amphiphilic structure is restricted by cyclization. Minimal conformational change upon target binding has been reported.

Polymyxin E (PME; fa-BTBBBBLLBBT, where fa=fatty acyl chain and B=diaminobutyrate; peptide is cyclized via the side chain of B4; SEQ ID No: 4) is a cyclic peptide possessing a hydrophobic terminus. Recent reports indicate that minor changes in conformation (loss of backbone turns) when polymyxins bind to target molecules.

With the exception of bactenecin, the above peptides have been documented to undergo structural changes upon binding to target membranes and membrane components. This characteristic is critical to detection of bound targets in a "reagent-less" manner—namely, the changes in peptide structure upon target binding will alter the localized environment of an attached porphyrin moiety, leading to a change in optical properties of the pendant porphyrin.

Attachment

Direct covalent attachment of C1TPP and C1S3TPP to the above peptides was accomplished with carbodiimide-mediated coupling, using ratios of 1 peptide: 1.1-1.2 porphyrin. When coupling under non-aqueous coupling (most useful for C1 TPP), a 1-2 molar excesses of 1-ethyl-3-(3-dimethylaminopropyl) carbodiimide hydrochloride (EDC) and N-hydroxysulfosuccinimide (NHS) were used to mediate the reaction. When coupling under aqueous conditions (C1S3TPP), EDC and NHS were added to the peptide/porphyrin mix at four timepoints, each time using a 5-fold molar excess of each. After completion of the coupling reactions (>>2 hours), reaction mixes were diluted with water and were dialyzed exhaustively against water and phosphate-buffered saline (PBS). Although only carbodiimide-based coupling has been used to date to conjugate porphyrins to the peptides, other linking chemistries can also be used (e.g., "click" chemistry, homo- and hetero bifunctional crosslinkers), provided suitable chemical moieties are present on the peptides and/or porphyrin components.

Absorbance and Fluorescence Characterization

Figure 1A:
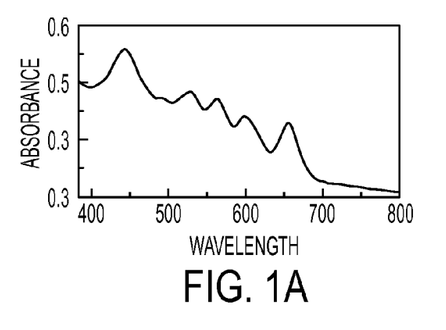
FIGS. 1A and 1B show absorbance (A) and fluorescence (B) characteristics of 5-mono(4-carboxyphenyl)-10,15,20-triphenyl porphine ($C_1$TPP) in aqueous solution with dimethylsulfoxide (DMSO).
Figure 1B:
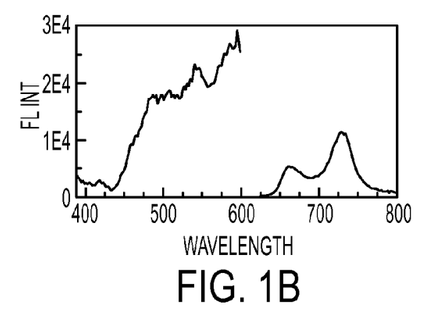
Figure 2A:
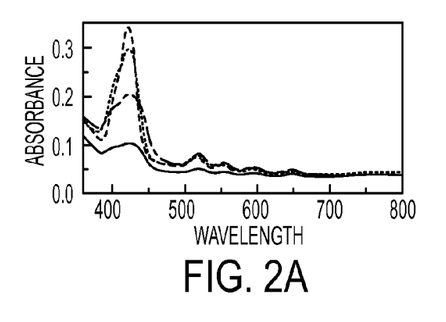
FIGS. 2A-D present the absorbance and fluorescence characteristics for each of four porphyrin/peptide constructs, showing absorbance (A, B) and fluorescence (C, D) characteristics of the porphyrin modified antimicrobial peptides in aqueous solution: C1-Bac (long dashes) with DMSO, $C_1$-CeMe(L) (short dashes), C1-PME (solid line) with DMSO, $C_1$-Ind (dots). C1 represents $C_1$TPP while Bac, CeMe(L), PME, and Ind represent Bactenecin, a Cecropin A-melittin hybrid, Polymyxin E, and Indolicidin, respectively.
Figure 2B:
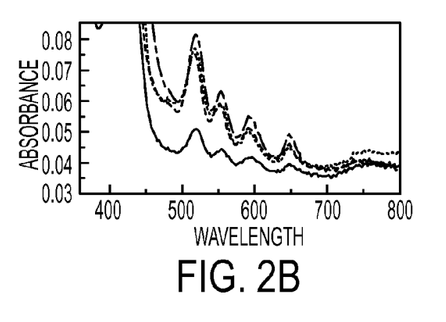
Figure 2C:
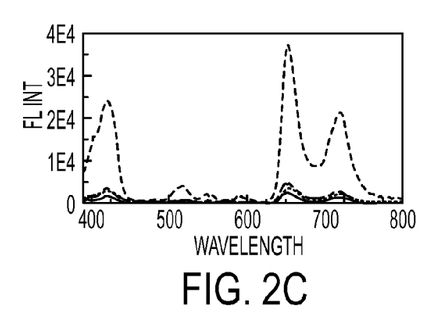
Figure 2D:
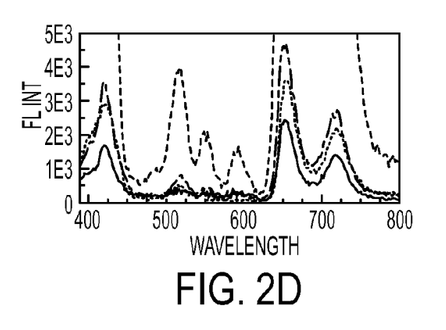

In order for porphyrin-modified AMPs to provide a useful mechanism for detection of microbial targets, it is critical that the spectrophotometric characteristics of the porphyrin modification be influenced by the antimicrobial peptide. Interaction of a porphyrin with the bacterial target will likely result in changes in the spectrophotometric characteristics, but these will be nonspecific changes. The specificity in the construct results from the specificity of the antimicrobial peptide. When the antimicrobial peptide interacts with a target there is a conformation change upon binding. The goal is to design a construct in which this conformational change leads to spectrophotometric changes in the associated porphyrin, as seen in FIGS. 1A and 1B. The first characterization of the constructs is an evaluation of the impact of the interaction of the porphyrin with the antimicrobial peptide on the spectrophotometric characteristics of the porphyrin. FIG. 1 shows absorbance (A) and fluorescence (B) characteristics of $C_1$TPP in aqueous solution with DMSO.

$C_1$TPP and $C_1$TPP-modified antimicrobial peptides were evaluated in a microtiter plate format using a Tecan XSafire monochromator-based microplate reader. Absorbance measurements were collected between 380 and 800 nm at 2 nm resolution. Fluorescence measurements were collected at 2 nm resolution for emission between 550 and 800 nm with excitation at 415 nm and for excitation between 385 and 619 nm with emission at 730 nm. FIGS. 2A-2D present the absorbance and fluorescence characteristics for each of the four constructs, showing absorbance (A, B) and fluorescence (C, D) characteristics of the porphyrin modified antimicrobial peptides in aqueous solution: C1-Bac (long dashes) with DMSO, $C_1$-CeMe(L) (short dashes), C1-PME (solid line) with DMSO, $C_1$-Ind (dots).

$C_1$TPP is minimally soluble in water. With the addition of 10% dimethylsulfoxide (DMSO, final concentration in experiment), the solubility can be increased somewhat. It is still insufficient to resolve spectrophotometric characteristics with no indication of stacking as evidenced by the low absorbance intensity and indistinct bands in both absorbance and fluorescence characteristics (FIGS. 1A and 1B). When the porphyrin was coupled to the antimicrobial peptides, significantly improved spectrophotometric characteristics were observed. In FIGS. 2A-2D, the more traditional Soret and Q-bands in the absorbance spectra are evident, and the expected two peak fluorescence emission spectra are observed. C1-CeMe(L) and C1-Ind constructs were soluble in water. Phase separation was observed for C1-PME, and C1-Bac precipitated from aqueous solution. Addition of 10% DMSO was sufficient to maintain the solubility of both tracers for experimental analysis. Each of the constructs has unique peak positions as well as varying extinction coefficients for the Soret and Q-bands. Fluorescence emission is also uniquely varying amongst the tracers. These factors tend to indicate the formation of unique complexes providing the potential desired for these materials.

Here, one porphyrin has been used to modify to four antimicrobial peptides. This should in no way be viewed as a limit on the approach; it is rather a first step in proof-of-concept. The porphyrins are required only to have appropriate groups providing sites for covalent attachment to the antimicrobial peptides. Phthalocyanines could be applied similarly. In addition, while this porphyrin has no metal in the central coordination site, hundreds of variants with unique spectrophotometric characteristics could be generated through metal complex formation with the four porphyrin-modified AMPs described here.

Interactions with Bacterial Targets

Figure 3A:
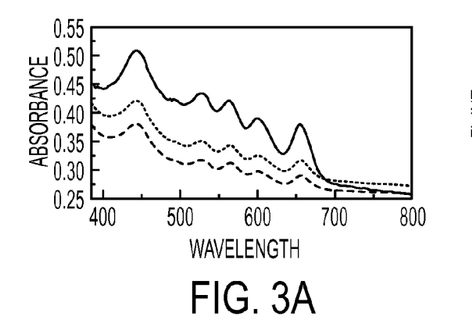
FIGS. 3A and 3B present data for the interaction between $C_1$TPP and two cell types, with absorbance (A) and fluorescence (B) spectra for $C_1$TPP in water (black, 10% DMSO) and in the presence of E. coli (dashes) and B. globigii (dots) at $1.8 \times 10^6$ cfu/mL.
Figure 3B:
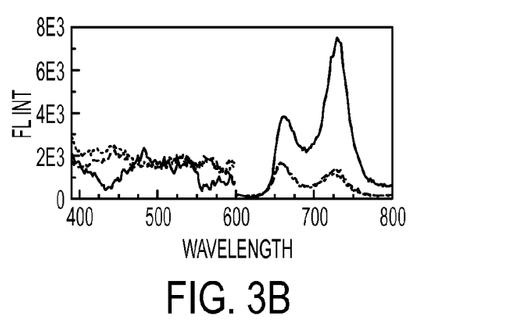

The microtiter plate format described above was utilized for analysis of interactions between the porphyrin-AMP constructs and bacterial cells, specifically, E. coli and B. globigii. The bacterial cells utilized were collected at mid-log phase growth and rinsed with water to remove growth media. They were then resuspended in water at approximately $3.5 \times 10^7$ cfu/mL. Analyses looked at changes in fluorescence and absorbance for fixed cell concentrations with varying tracer concentrations as well as for fixed tracer concentrations with varying cell concentrations. FIGS. 3A and 3B present data for the interaction between $C_1$TPP and the two cell types, with absorbance (A) and fluorescence (B) spectra for $C_1$TPP in water (black, 10% DMSO) and in the presence of E. coli (dashes) and B. globigii (dots) at $1.8 \times 10^6$ cfu/mL. The interaction of $C_1$TPP with these cells did not produce concentration dependent changes in the absorbance or fluorescence characteristics of the porphyrin. An overall quench was noted in the fluorescence emission spectra of the porphyrin in the presence of the cells.

Figure 4A:
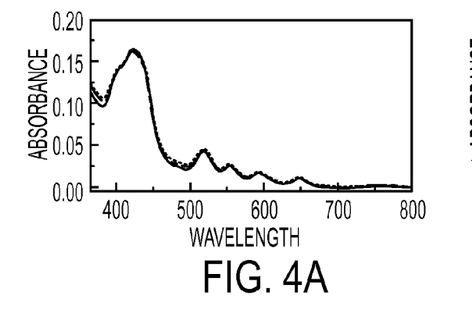
FIGS. 4A-4D show interaction of C1-Bac with bacterial cells. Absorbance (A) and fluorescence (C) spectra for C1-Bac in water (black, 10% DMSO) and in the presence of E. coli (dashes) and B. globigii (dots) at $1.8 \times 10^6$ cfu/mL. Also shown are the difference absorbance (B) and fluorescence (D) calculated as the point-by-point subtraction of the spectrum of the tracer from the spectrum obtained in the presence of target.
Figure 4B:
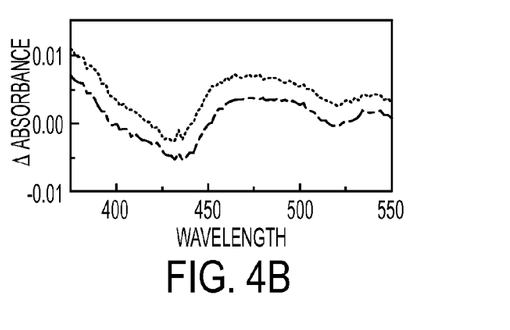
Figure 4C:
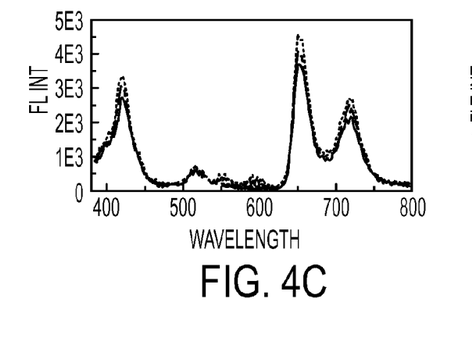
Figure 4D:
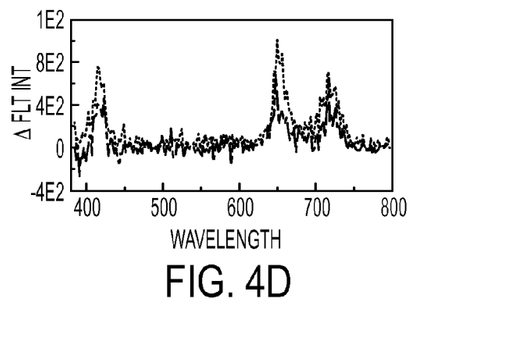
Figure 5A:
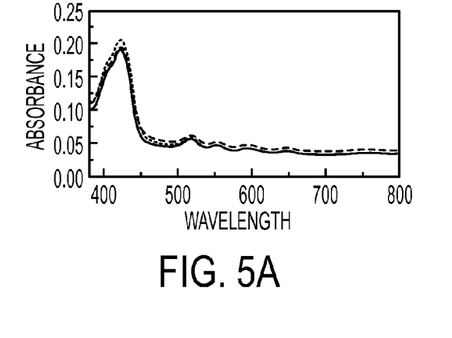
FIGS. 5A-D show interaction of C1-Ind with bacterial cells. Absorbance (A) and fluorescence (C) spectra for C1-Ind in water (solid line) and in the presence of E. coli (dashes) and B. globigii (dots) at $1.8 \times 10^6$ cfu/mL. Also shown are the difference absorbance (B) and fluorescence (D) calculated as the point-by-point subtraction of the spectrum of the tracer from the spectrum obtained in the presence of target.
Figure 5B:
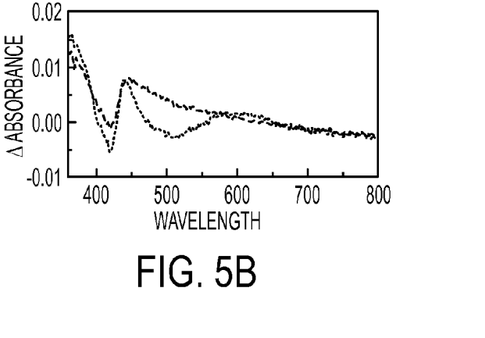
Figure 5C:
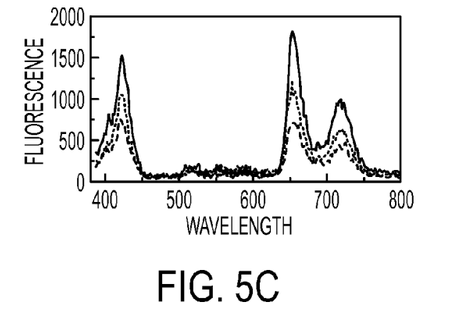
Figure 5D:
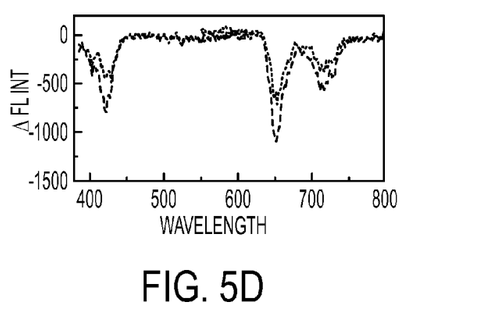
Figure 6A:
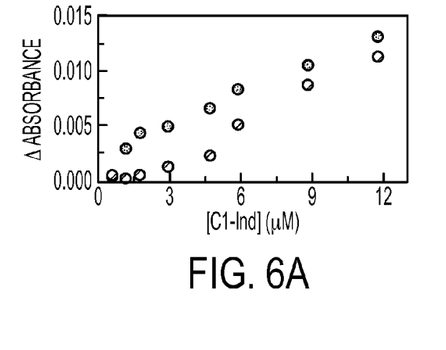
FIGS. 6A and B show concentration dependence of cell/tracer interactions. (A) Change in absorbance (peak minus trough) for the interaction of C1-Ind with E. coli (slash filled marks) and B. globigii (dotted filled marks) at $1.8 \times 10^6$ cfu/mL. (B) Change in absorbance (trough depth) for the interaction of C1-CeMe with bacterial cells.
Figure 6B:
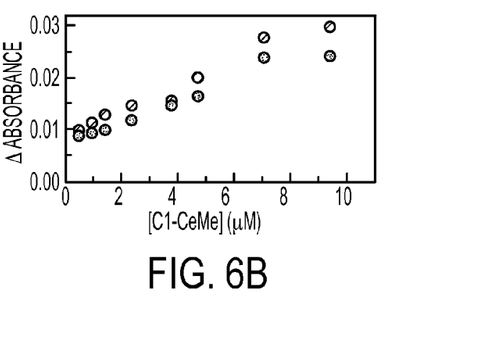
Figure 7A:
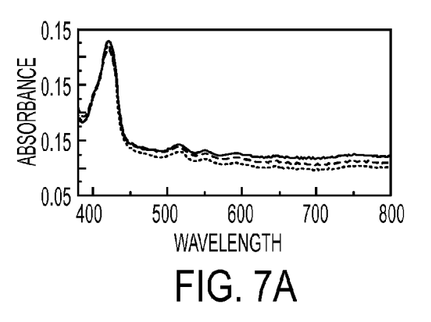
FIGS. 7A-D show interaction of C1-CeMe(L) with bacterial cells. Absorbance (A) and fluorescence (C) spectra for C1-CeMe(L) in water (solid line) and in the presence of E. coli (dashes) and B. globigii (dots) at $1.8 \times 10^6$ cfu/mL. Also shown are the difference absorbance (B) and fluorescence (D) calculated as the point-by-point subtraction of the spectrum of the tracer from the spectrum obtained in the presence of target.
Figure 7B:
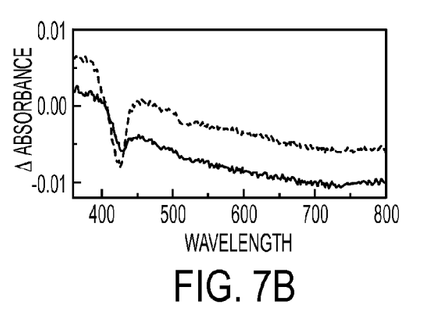
Figure 7C:
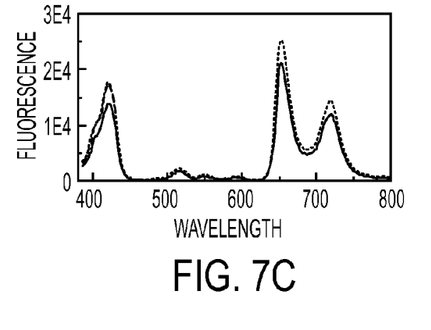
Figure 7D:
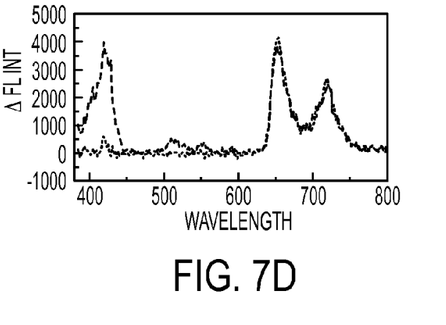
Figure 8A:
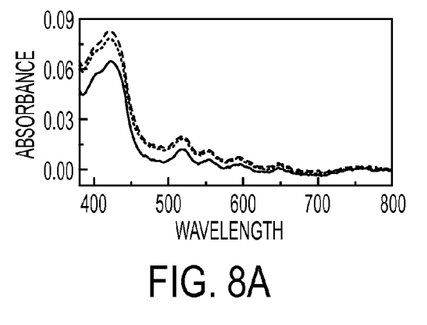
FIGS. 8A-D show interaction of C1-PME with bacterial cells. Absorbance (A) and fluorescence (C) spectra for C1-PME in water (solid line) and in the presence of E. coli (dashes) and B. globigii (dots) at $1.8 \times 10^6$ cfu/mL. Also shown are the difference absorbance (B) and fluorescence (D) calculated as the point-by-point subtraction of the spectrum of the tracer from the spectrum obtained in the presence of target.
Figure 8B:
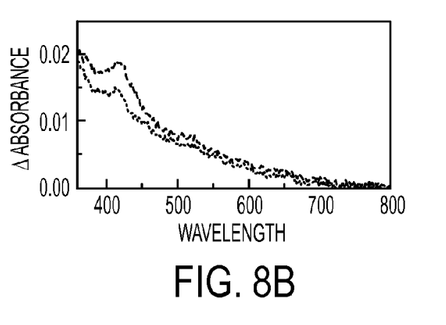
Figure 8C:
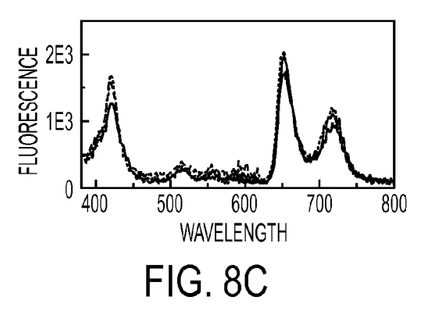
Figure 8D:
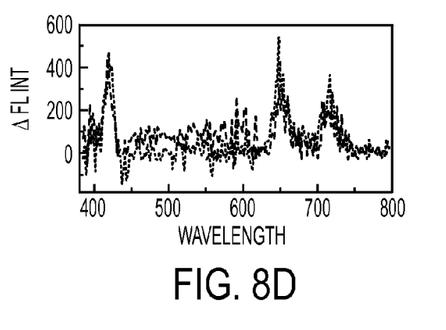
Figure 9A:
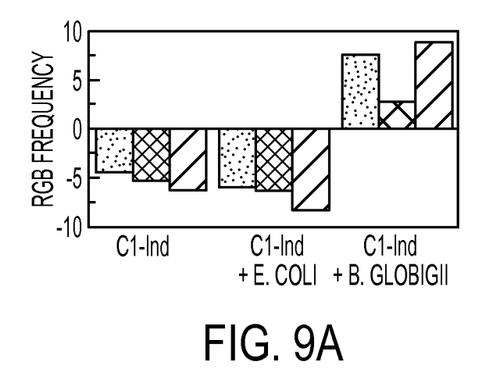
FIGS. 9A and 9B show reflectance based detection. (A) Red, green, and blue (RGB) reflectance values for C1-Ind in the absence and presence of E. coli or B. globigii. These measurements have been corrected for background signal intensity based on measurements collected for water and for each type of cell at the relevant concentrations. (B) Difference RGB values for the interaction of C1-Ind with bacterial cells. Red is represented by dotted fill, green by crossed fill, and blue by fill with diagonal lines.
Figure 9B:
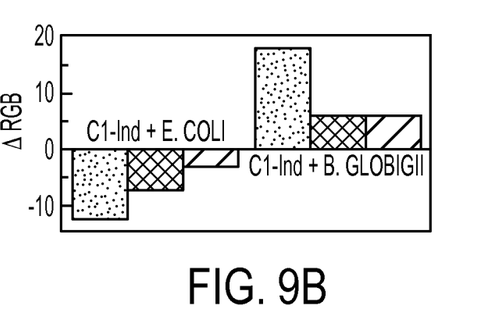

Spectrophotometric changes for the porphyrin-AMP constructs were specific and dependent on the construct considered, the type of bacteria, and the concentrations of the two components. In the case of $C_1$TPP-bactenecin (C1-Bac) both E. coli and B. globigii produced a peak/trough pair at 476/432 nm in the Soret region of the absorbance difference spectrum for the construct (FIGS. 4A and 4B). Changes in fluorescence were noted for only the highest concentrations of tracer used. These increases in fluorescence are likely related to solubility rather than specific interactions. The similarity in changes noted for E. coli and B. globigii, in both fluorescence and absorbance, would tend to support this idea. Changes in absorbance and fluorescence for C1-Ind are not indicative of improved solubility upon interaction with the cells; C1-Ind was water soluble in the range of concentrations considered. FIGS. 5A-D present the absorbance and fluorescence characteristics for C1-Ind. While changes in absorbance for the Soret region were noted at similar peak positions, the shape of the changes and the concentration dependence of the interaction were distinctly different for the two types of bacteria. The interaction of C1-Ind with *B. globigii* produced a peak at 600 nm in addition to the Soret region peak/trough pair at 444/418 nm (FIG. 5). In addition, the changes produced in the absorbance spectrum were of larger intensity for the interaction of C1-Ind with *B. globigii* than that observed for *E. coli* (FIGS. 6A and B).

The interaction of C1-CeMe(L) with the two bacterial targets produced distinct results in both the absorbance and fluorescence spectra. For both targets, a trough was observed in the Soret region of the absorbance spectrum at 425 nm for *E. coli* and 432 nm for *B. globigii* (FIGS. 7A and 7C). The changes in fluorescence for the interaction of the two targets with C1-CeMe were strikingly different in the excitation spectra region. Difference fluorescence for *B. globigii* was flat for all concentrations evaluated (FIGS. 7B and 7D). The concentration dependence for the change in Soret region absorbance is presented in FIGS. 6A and B. Changes in the spectrum of C1-PME (FIGS. 8A-D) were small for the range of concentrations evaluated; however, there is sufficient evidence to suggest that, if solubility issues were addressed, interaction with the targets would lead to changes in the spectrophotometric characteristics of this indicator.

Absorbance and fluorescence type measurements are commonly employed for detection applications. The materials described here are applicable to either of those methods, but also lend themselves to application in a reflectance-type format. This type of format allows for monitoring of spectrophotometric characteristics without the complication of sample streams that traverse the illumination pathway. In order to demonstrate this potential, a TAOS TCS3200 RGB sensor chip in a reflectance configuration was used to monitor RGB color values for C1-Ind in the presence and absence of bacterial cells (in aqueous solution). As shown in FIGS. 9A and 9B, changes in reflectance upon exposure to *E. coli* or *B. globigii* cells were unique for the indicator. Though this experiment provides only proof-of-concept for the approach, utilization of this type of indicator for reagent-less detection of bacterial targets is clearly demonstrated. The implementation of the indicators could use a reflectance array format similar to that described by Rakow et al. (ref. 21) for chemical detection based on a fingerprint type response from several different indicators.

Porphyrin-modified antimicrobial peptides as described here provide a potential avenue for facilitation of distributed and autonomous sensing applications. They address the long-standing challenge of detecting biological targets in a reagent-less format. They also offer the potential for detection of not only known but unknown and potentially uncharacterized threats.

Current efforts in threat detection are focused on a multi-tiered approach in which rapid devices of lower sensitivity provide initial threat indication and more complex devices are utilized for confirmation. The potential for application of the described indicators in a reagent-less format utilizing absorbance, fluorescence, or reflectance based sensing makes them uniquely suited to the lowest, most highly distributed, tier of this approach.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Kulagina, N. V., et al., *Antimicrobial peptides: New recognition molecules for detecting botulinum toxins*. Sensors, 2007. 7(11): p. 2808-2824.
2. Kulagina, N. V., et al., *Antimicrobial peptide-based array for Escherichia coli and Salmonella screening*. Analytica Chimica Acta, 2006. 575(1): p. 9-15.
3. Ngundi, M. M., et al., *Nonantibody-based recognition: alternative molecules for detection of pathogens*. Expert Review of Proteomics, 2006. 3(5): p. 511-524.
4. North, S. H., et al., *Surface immobilization chemistry influences peptide-based detection of lipopolysaccharide and lipoteichoic acid*. Journal of Peptide Science, 2012. 18(6): p. 366-372.
5. Taitt, C. R., et al., *Array Biosensor for Toxin Detection: Continued Advances*. Sensors, 2008. 8(12): p. 8361-8377.
6. Baldini, L., et al., *Pattern-based detection of different proteins using an array of fluorescent protein surface receptors*. Journal of the American Chemical Society, 2004. 126(18): p. 5656-5657.
7. Tsou, L. K., R. K. Jain, and A. D. Hamilton, *Protein surface recognition by porphyrin-based receptors*. Journal of Porphyrins and Phthalocyanines, 2004. 8(1-3): p. 141-147.
8. Zhou, H. C., et al., *Pattern recognition of proteins based on an array of functionalized porphyrins*. Journal of the American Chemical Society, 2006. 128(7): p. 2421-2425.
9. White, B. J. and H. J. Harmon, *Interaction of monosulfonate tetraphenyl porphyrin, a competitive inhibitor, with acetylcholinesterase*. Biosens Bioelectron, 2002. 17(6-7): p. 463-469.
10. White, B. J. and H. J. Harmon, *Optical solid-state detection of organophosphates using organophosphorus hydrolase*. Biosens Bioelectron, 2005. 20(10): p. 1977-1983.
11. Kuciauskas, D., et al., *Exciton annihilation and energy transfer in self-assembled peptide-porphryin complexes depends on peptide secondary structure*. J Phys Chem B, 2010. 114: p. 16029-16035.
12. Harmon, H. J., *Specific Visible Spectral Changes Induced by Guanine Binding to Cytosine-derivatized porphyrin*. J. Porphyrins Phthalocyanines, 2002. 6: p. 73-77.
13. Dosselli, R., et al., *Synthesis, Characterization, and Photoinduced Antibacterial Activity of Porphyrin-Type Photosensitizers Conjugated to the Antimicrobial Peptide Apidaecin 1b*. Journal of Medicinal Chemistry, 2012.
14. Dosselli, R., et al., *Porphyrin-apidaecin conjugate as a new broad spectrum antibacterial agent*. ACS Med Chem Lett, 2010. 1: p. 35-38.
15. Liu, F., et al., *Lipopolysaccharide neutralizing peptide-porphyrin conjugates for effective photoinactivation and intracellular imaging of Gram-negative bacteria strains*. Bioconjug Chem, 2012. 23: p. 1639-1647.
16. Sibrian-Vasquez, M., T. Jensen, and M. Vicente, *Synthesis, characterization, and metabolic stability of por-* phyrin-peptide conjugates bearing bifunctional signaling sequences. J Med Chem, 2008. 51: p. 2915-2923.

17. Hasan, T., M. Hamblin, and N. Soukos, *Photosensitizer conjugates for pathogen targeting*, USPTO, Editor. 2007, The General Hospital Corporation: USA.
18. Bourre, L., et al., *Effective photoinactivation of Gram-positive and Gram-negative bacterial strains using an HIV-1 Tat peptide-porphyrin conjugate*. Photochemical & Photobiological Sciences, 2010. 9(12): p. 1613-1620.
19. Reddi, E., et al., *Photophysical properties and antibacterial activity of meso-substituted cationic porphyrins* Photochem Photobiol, 2002. 75: p. 462-470.
20. Pristovšek, P. and J. Kidrič, *Solution Structure of Polymyxins B and E and Effect of Binding to Lipopolysaccharide: An NMR and Molecular Modeling Study*. Journal of Medicinal Chemistry, 1999. 42(22): p. 4604-4613.
21. Rakow, N. A. and K. S. Suslick, *A colorimetric sensor array for odour visualization*. Nature, 2000. 406(6797): p. 710-713.

ADDITIONAL BACKGROUND DOCUMENTS

Patents

Harmon. Broad spectrum bio-detection of nerve agents, organophosphates, and other chemical warfare agents. U.S. Pat. No. 6,821,738 B2; November 2004
Hasan, Hamblin, Soukos. Photosensitizer conjugates for pathogen targeting. U.S. Pat. No. 7,268,155; September 2007

Patent Applications

McAlpine, Mannoor. Biosensor for detecting target, preferably Escherichia coli, has peptide immobilized on sensing component . . . US Patent Application US2012156688-A1
Kulagina, et al. Biochemical identification method useful for detecting biological target such as bacteria . . . US Patent Application US2006281074-A1
Pamgene, et al. Screening cellular responses of cellular components comprises incubating test compounds with cellular components . . . US Patent Application US2005255445-A1

Publications

North S H, Wojciechowski J, Chu V, Taitt C R (2012) Journal of Peptide Science 18: 366-372.
Taitt C R, Shriver-Lake L C, Ngundi M M, Ligler F S (2008) Sensors 8: 8361-8377.
Kulagina N V, Taitt C R, Anderson G P, Ligler F S, Shaffer K M (2007) Sensors 7: 2808-2824.
Ngundi M M, Kulagina N V, Anderson G P, Taitt C R (2006) Expert Review of Proteomics 3: 511-524.
Kulagina N V, Taitt C R, Shaffer K M, Anderson G P, Ligler F S (2006) Analytica Chimica Acta 575: 9-15.
Harmon H J (2002) J Porphyr Phthalocyan 6: 73-7.
Zhou H, Baldini L, Hong J, Wilson A J, Hamilton A D (2006) JACS 128: 2421-5.
Baldini L, Wilson A J, Hong J, Hamilton A D (2004) JACS 126: 5656-7.
White B J, Hamon H J (2002) Biosens Bioelectron 17:463-9.

What is claimed is:

1. A method of detecting bacterial cells, comprising:
providing a porphyrin-modified antimicrobial peptide comprising a porphyrin covalently attached to an antimicrobial peptide;
contacting the porphyrin-modified antimicrobial peptide in a microtiter plate with the bacterial cells, thereby causing a conformational change in the porphyrin-modified antimicrobial peptide; and
detecting with a microtiter plate reader a change in fluorescence and/or absorbance of the porphyrin-modified antimicrobial peptide caused by the conformational change, corresponding to a presence or absence of the bacterial cells,
wherein the method is operable to detect the bacterial cells without use of an additional optically-active reagent,
wherein the porphyrin is 5-mono(4-carboxyphenyl)-10,15,20-triphenyl porphine and the antimicrobial peptide is covalently attached to the porphyrin via carbodiimide-mediated coupling, and
wherein said antimicrobial peptide is Indolicidin or Cecropin A-melittin hybrid peptide CeMe(L).

* * * * *